United States Patent
Katzir et al.

(10) Patent No.: US 10,571,406 B2
(45) Date of Patent: Feb. 25, 2020

(54) METHOD OF PERFORMING METROLOGY OPERATIONS AND SYSTEM THEREOF

(71) Applicant: Applied Materials Israel Ltd., Rehovot (IL)

(72) Inventors: Ron Katzir, Tel Aviv (IL); Imry Kissos, Kiryat-Ono (IL); Lavi Shachar, Tel Aviv (IL); Amit Batikoff, Petach Tikva (IL); Shaul Cohen, Irus (IL); Noam Zac, Kfar Saba (IL)

(73) Assignee: Applied Materials Israel Ltd., Rehovot (IL)

( * ) Notice: Subject to any disclaimer, the term of this patent is extended or adjusted under 35 U.S.C. 154(b) by 0 days.

(21) Appl. No.: 16/179,700

(22) Filed: Nov. 2, 2018

(65) Prior Publication Data
US 2019/0121933 A1    Apr. 25, 2019

Related U.S. Application Data

(63) Continuation of application No. 15/460,078, filed on Mar. 15, 2017, now Pat. No. 10,120,973.

(51) Int. Cl.
*G01N 21/95* (2006.01)

(52) U.S. Cl.
CPC ................. *G01N 21/9501* (2013.01)

(58) Field of Classification Search
CPC .................................................. G06F 17/5081
USPC ........................................................ 716/136
See application file for complete search history.

(56) References Cited

U.S. PATENT DOCUMENTS

| 6,869,739 B1 | 3/2005 | Ausschnitt et al. |
| 7,175,940 B2* | 2/2007 | Laidig ....................... G03F 1/36 |
| | | 382/144 |
| 7,207,017 B1 | 4/2007 | Tabery et al. |
| 7,507,961 B2* | 3/2009 | Toyoda ................. G06T 7/0006 |
| | | 250/306 |
| 8,283,630 B2* | 10/2012 | Miyamoto ......... G01N 23/2251 |
| | | 250/307 |
| 8,432,441 B2 | 4/2013 | Fang et al. |
| 8,445,871 B2 | 5/2013 | Matsuoka et al. |
| 8,559,001 B2* | 10/2013 | Chang ................ G01N 21/9501 |
| | | 250/559.3 |

(Continued)

FOREIGN PATENT DOCUMENTS

| WO | WO2014081897 A1 | 5/2014 |
| WO | WO2015153872 A1 | 10/2015 |
| WO | WO2016010776 A1 | 1/2016 |

*Primary Examiner* — Suresh Memula
(74) *Attorney, Agent, or Firm* — Lowenstein Sandler LLP

(57) ABSTRACT

One or more metrology objects and one or more metrology operations may be identified. A design-based representation of a first metrology object of the one or more metrology objects may be received. Furthermore, an image-based representation of the first metrology object of the one or more metrology objects may be received where the one or more metrology operations include a first metrology operation associated with the first metrology object that is to be performed on the image-based representation of the first metrology object. The design-based representation of the first metrology object may be mapped with the image-based representation of the first metrology object. The first metrology operation may be performed based on the mapping.

20 Claims, 6 Drawing Sheets

Accommodating, in the memory, definitions of one or more metrology objects and one or more metrology operations, wherein at least one of the group consisting of the one or more metrology objects and the one or more metrology operations is defined with reference to design data (202)

Accommodating, in the memory, a representation group comprising a design-based representation of the specimen and an image-based representation of the specimen (204)

Mapping, by the processor, between the design-based representation of the at least first metrology object and the image-based representation of the at least first metrology object (206)

Performing, by the processor, the at least first metrology operation according to definition of the at least first metrology operation using the mapping (208)

(56) References Cited

U.S. PATENT DOCUMENTS

| | | | |
|---|---|---|---|
| 8,779,359 B2* | 7/2014 | Ogiso | G06T 7/001 |
| | | | 250/307 |
| 8,809,778 B2* | 8/2014 | Ogino | H01J 37/222 |
| | | | 250/306 |
| 9,041,795 B2 | 5/2015 | Fang et al. | |
| 9,100,553 B2 | 8/2015 | Fang et al. | |
| 9,251,581 B1 | 2/2016 | Chen et al. | |
| 9,282,293 B2 | 3/2016 | Fang et al. | |
| 2006/0288325 A1 | 12/2006 | Miyamoto et al. | |
| 2007/0187595 A1* | 8/2007 | Tanaka | G01N 23/2251 |
| | | | 250/307 |
| 2007/0280527 A1 | 12/2007 | Almogy et al. | |
| 2013/0204569 A1 | 8/2013 | Goren et al. | |
| 2013/0234020 A1* | 9/2013 | Ogino | H01J 37/222 |
| | | | 250/307 |
| 2013/0298088 A1* | 11/2013 | Lee | G03F 1/84 |
| | | | 716/52 |
| 2014/0086475 A1* | 3/2014 | Daneshpanah | G06T 7/001 |
| | | | 382/144 |
| 2014/0198975 A1* | 7/2014 | Nakagaki | G01N 23/2251 |
| | | | 382/149 |
| 2015/0041649 A1 | 2/2015 | Wang | |
| 2015/0069232 A1 | 3/2015 | Lin et al. | |
| 2015/0146967 A1 | 5/2015 | Miyamoto et al. | |
| 2015/0162249 A1 | 6/2015 | Ausschnitt et al. | |
| 2015/0212019 A1 | 7/2015 | Shishido et al. | |
| 2015/0278426 A1 | 10/2015 | Ning et al. | |
| 2016/0283617 A1 | 9/2016 | Bailey et al. | |
| 2016/0349742 A1 | 12/2016 | Dalla-Torre et al. | |
| 2017/0219928 A1 | 8/2017 | Heo et al. | |
| 2018/0113387 A1 | 4/2018 | Xiao et al. | |

* cited by examiner

METHOD OF PERFORMING METROLOGY OPERATIONS AND SYSTEM THEREOF

RELATED APPLICATION

This application is a continuation of U.S. patent application Ser. No. 15/460,078 filed on Mar. 15, 2017, the contents of which are hereby incorporated by reference.

TECHNICAL FIELD

The presently disclosed subject matter relates, in general, to the field of metrology of semiconductor fabrication, and more specifically, to methods and systems of performing metrology operations related to a specimen.

BACKGROUND

Current demands for high density and performance associated with ultra large scale integration of fabricated devices require submicron features, increased transistor and circuit speeds, and improved reliability. As semiconductor processes progress, pattern dimensions such as line width, and other types of critical dimensions, are continuously shrunken. Such demands require formation of device features with high precision and uniformity, which, in turn, necessitates careful monitoring of the fabrication process, including frequent and detailed inspections and metrology operations related to the devices while they are still in the form of semiconductor wafers.

The term "specimen" used in this specification should be expansively construed to cover any kind of wafer, masks, and other structures, combinations and/or parts thereof used for manufacturing semiconductor integrated circuits, magnetic heads, flat panel displays, and other semiconductor-fabricated articles.

The terms "inspection" and "Metrology" alternately used in this specification should be expansively construed to cover any kind of measuring characteristics and features in a specimen provided by using measurement tools during or after manufacture of the specimen to be inspected. By way of non-limiting example, the metrology process can include generating a measurement recipe and/or performing runtime measurement, for example by scanning (in a single or in multiple scans), reviewing, measuring and/or other operations provided with regard to the specimen or parts thereof using the same or different inspection tools. Measurement results such as measured images are analyzed for example, by employing image-processing techniques. Note that, unless specifically stated otherwise, the terms "inspection", "metrology" or their derivatives used in this specification are not limited with respect to measurement technology, measurement resolution or size of inspection area.

A variety of metrology tools includes, by way of non-limiting example, scanning electron microscopes (SEM), tunneling electron microscope (TEM), atomic force microscopes (AFM), optical metrology (OCD) and inspection tools, etc.

There is a need in the art to improve the process of metrology, for example by improving the utilization of design data; by improving the preparation of metrology recipes; or by improving the definition of metrology objects and metrology operations used for metrology.

GENERAL DESCRIPTION

In accordance with certain aspects of the presently disclosed subject matter, there is provided a method of performing metrology operations on at least one representation of a specimen using a processor operatively connected to a memory, the method comprising: accommodating, in the memory, definitions of one or more metrology objects and one or more metrology operations, wherein at least one of the group consisting of the one or more metrology objects and the one or more metrology operations is defined with reference to design data; accommodating, in the memory, a representation group comprising a design-based representation of the specimen and an image-based representation of the specimen; wherein the design-based representation of the specimen comprises design-based representation of at least first metrology object of the one or more metrology objects and the image-based representation of the specimen comprises image-based representation of the at least first metrology object of the one or more metrology objects, and wherein the one or more metrology operations include at least first metrology operation, the at least first metrology operation being defined to be related to the at least first metrology object and to be performed on at least the image-based representation of the specimen; mapping, by the processor, between the design-based representation of the at least first metrology object and the image-based representation of the at least first metrology object; and performing, by the processor, the at least first metrology operation according to definition of the at least first metrology operation using the mapping.

In addition to the above features, the method according to this aspect of the presently disclosed subject matter can comprise one or more of features (i) to (xv) listed below, in any desired combination or permutation which is technically possible:

(i). The design data can be the design-based representation of the specimen, and the one or more metrology operations can be defined related to at least one of the metrology objects.

(ii). The design data can be pre-acquired design data, the one or more metrology objects can be defined on the pre-acquired design data, and at least one of the metrology operations can be defined related to the one or more metrology objects. The method can further comprise: searching on the design-based representation of the specimen to identify the at least first metrology object.

(iii). The one or more metrology objects can include one or more initial objects each initially defined on the design data or image data.

(iv). The one or more metrology objects can further include one or more derived objects resulted from performing at least one of the metrology operations defined related to the initial objects, and the one or more metrology operations can include at least one operation defined related to the derived objects.

(v). The one or more metrology objects can include one or more of the following: structural elements, virtual objects, and ghost objects, wherein the virtual objects are metrology objects that do not have an original design-based representation thereof, and ghost objects are metrology objects that only have design-based representation thereof.

(vi). The one or more metrology operations can be selected from a group comprising: search operation, measurement operation, and Region Of Interest (ROI) operation.

(vii). The measurement operation can be selected from a group comprising: Area, Critical Dimension (CD), Distance, Center of Gravity (CoG), Gray Level (GL), Contact Hole Analysis (CHA), 'Distance from image to design', and Arithmetic calculations.

(viii). The one or more metrology objects can be defined on the design-based representation of the specimen and the metrology operations can be defined to be performed on the image-based representations of the specimen, or on both the image-based representations of the specimen and the design-based representation of the specimen.

(ix). The one or more metrology objects can be defined on the image-based representations of the specimen and the metrology operations can be defined to be performed on both the image-based representations of the specimen and the design-based representation of the specimen.

(x). The mapping can be performed by registering the image-based representations of the specimen with the design-based representation of the specimen to obtain position calibration data, identifying pairs of corresponding design-based representation and image-based representation of the at least first metrology object using the position calibration data and assigning a unique identifier to each of the pairs.

(xi). The definitions of one or more metrology operations can include a representation to perform the one or more metrology operations which is determined by one or more of the following factors: the type of the metrology operations, a representation where the metrology objects related to the metrology operations are defined and one or more additional parameters defined by a user.

(xii). At least one of the metrology objects is associated with an attribute of context indicative of a parent object thereof.

(xiii). At least second metrology object of the one or more metrology objects can have only a design-based representation thereof on the design-based representation of the specimen, and at least second metrology operation of the one or more metrology operations can be defined related to the at least second metrology object and to be performed on the image-based representation or on both the design-based representation of the specimen and the image-based representation. The method can comprise:

registering, by the processor, the design-based representation of the specimen and the image-based representation of the specimen to obtain position calibration data;

identifying, by the processor, a position indication of the at least second metrology object on the image-based representation of the specimen using the position calibration data; and performing, by the processor, at least second metrology operation of the one or more metrology operations related to the at least second metrology object according to definition of the at least second metrology operation using the position indication.

(xiv). The one or more metrology objects can include at least one defect object having only an image-based representation thereof on the image-based representation of the specimen, and at least third metrology operation of the one or more metrology operations can be defined related to the at least one defect object and to be performed on both the image-based representation and the design-based representation of the specimen. The method can comprise:

registering, by the processor, the design-based representation of the specimen and the image-based representation of the specimen to obtain position calibration data;

identifying, by the processor, a position indication of the at least one defect object on the design-based representation of the specimen using the position calibration data; and performing, by the processor, the at least third metrology operation on both the image-based representation and the design-based representation of the specimen using the position indication.

In accordance with another aspect of the presently disclosed subject matter, there is provided a computerized system capable of generating performing metrology operations on at least one representation of a specimen, the system comprising a processing circuitry that comprises a processor and a memory operatively coupled thereto, wherein: i) the memory is configured to: store definitions of one or more metrology objects and one or more metrology operations, wherein at least one of the group consisting of the one or more metrology objects and the one or more metrology operations is defined with reference to design data; and store a representation group comprising a design-based representation of the specimen and an image-based representation of the specimen; wherein the design-based representation of the specimen comprises design-based representation of at least first metrology object of the one or more metrology objects and the image-based representation of the specimen comprises image-based representation of the at least first metrology object of the one or more metrology objects, and wherein the one or more metrology operations include at least first metrology operation, the at least first metrology operation being defined to be related to the at least first metrology object and to be performed on at least the image-based representation of the specimen; and ii) the processing circuitry is configured to: map between the design-based representation of the at least first metrology object and the image-based representation of the at least first metrology object; and perform the at least first metrology operation according to definition of the at least first metrology operation using the mapping.

This aspect of the disclosed subject matter can comprise one or more of features (i) to (xiv) listed above with respect to the method, mutatis mutandis, in any desired combination or permutation which is technically possible.

In accordance with another aspect of the presently disclosed subject matter, there is provided a non-transitory computer readable storage medium tangibly embodying a program of instructions that, when executed by a computer, cause the computer to perform a method of generating performing metrology operations on at least one representation of a specimen, the method comprising: accommodating, in the memory, definitions of one or more metrology objects and one or more metrology operations, wherein at least one of the group consisting of the one or more metrology objects and the one or more metrology operations is defined with reference to design data; accommodating, in the memory, a representation group comprising a design-based representation of the specimen and an image-based representation of the specimen; wherein the design-based representation of the specimen comprises design-based representation of at least first metrology object of the one or more metrology objects and the image-based representation of the specimen comprises image-based representation of the at least first metrology object of the one or more metrology objects, and wherein the one or more metrology operations include at least first metrology operation, the at least first metrology operation being defined to be related to the at least first metrology object and to be performed on at least the image-based representation of the specimen; mapping, by the processor, between the design-based representation of the at least first metrology object and the image-based representation of the at least first metrology object; and performing, by the processor, the at least first metrology operation according to definition of the at least first metrology operation using the mapping.

This aspect of the disclosed subject matter can comprise one or more of features (i) to (xiv) listed above with respect to the method, mutatis mutandis, in any desired combination or permutation which is technically possible.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "accommodating", "defining", "mapping", "performing", "registering", "identifying", "assigning", "associating" or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example, the metrology operation system and parts thereof as well as the processing circuitry therein disclosed in the present application.

The terms "non-transitory memory" and "non-transitory storage medium" used herein should be expansively construed to cover any volatile or non-volatile computer memory suitable to the presently disclosed subject matter.

The term "defect" used in this specification should be expansively construed to cover any kind of abnormality or undesirable feature or void formed on or within a specimen.

The term "design data" used in the specification should be expansively construed to cover any data indicative of hierarchical physical design (layout) of a specimen. Design data can be provided by a respective designer and/or can be derived from the physical design (e.g. through complex simulation, simple geometric and Boolean operations, etc.). Design data can be provided in different formats as, by way of non-limiting examples, GDSII format, OASIS format, etc. Design data can be presented in vector format, grayscale intensity image format or otherwise.

It is appreciated that, unless specifically stated otherwise, certain features of the presently disclosed subject matter, which are described in the context of separate embodiments, can also be provided in combination in a single embodiment. Conversely, various features of the presently disclosed subject matter, which are described in the context of a single embodiment, can also be provided separately or in any suitable sub-combination. In the following detailed description, numerous specific details are set forth in order to provide a thorough understanding of the methods and apparatus.

Figure 1:
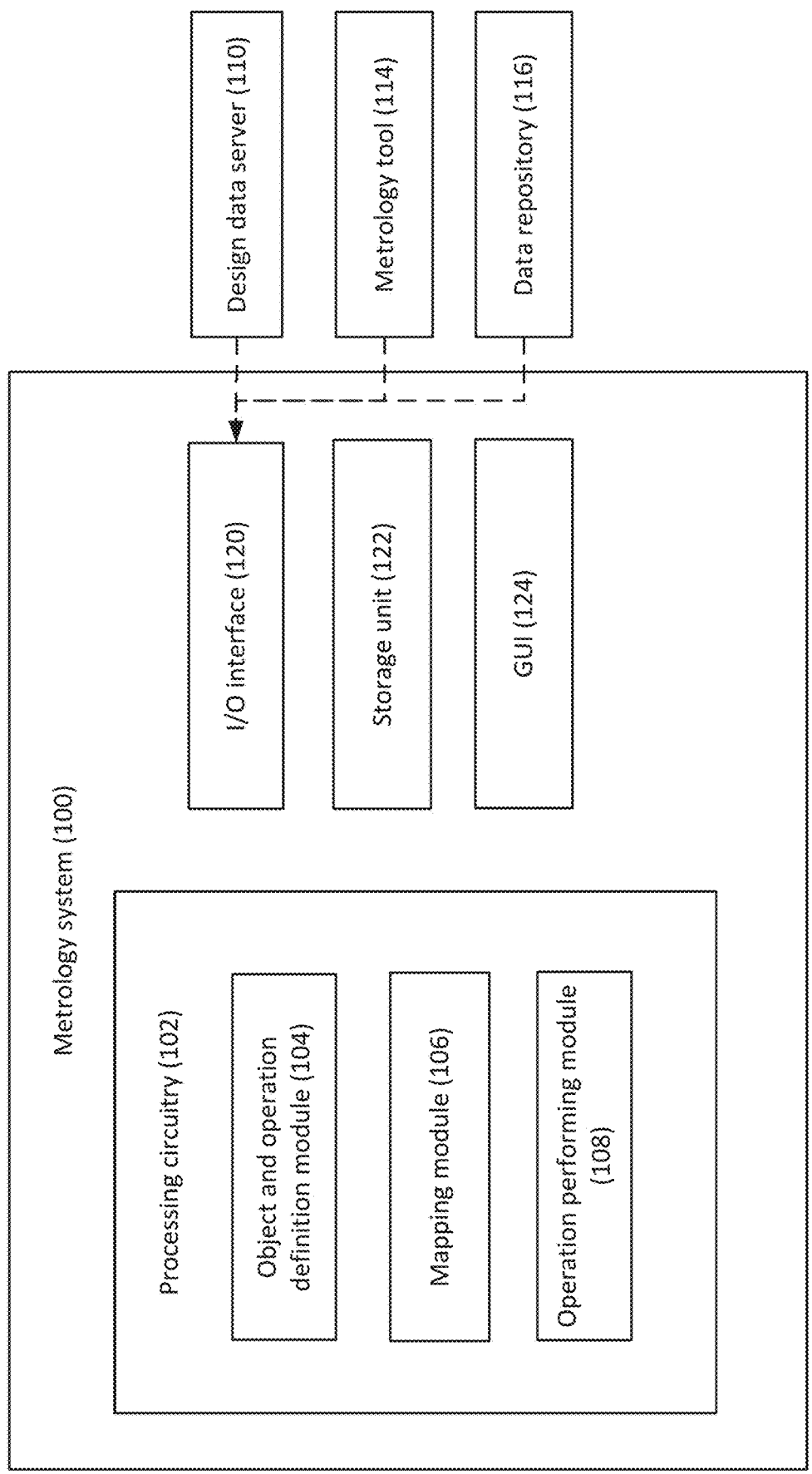
FIG. 1 illustrates a block diagram of a metrology system in accordance with certain embodiments of the presently disclosed subject matter.

Bearing this in mind, attention is drawn to FIG. 1 illustrating a block diagram of a metrology system in accordance with certain embodiments of the presently disclosed subject matter. The metrology system 100 illustrated in FIG. 1 can be used for defining and performing metrology operations on at least one representation of a specimen (e.g. of a wafer and/or parts thereof) as a part of specimen fabrication process or as a process after fabrication. The illustrated metrology system 100 is a computer-based system capable of defining and performing metrology operations related to a specimen using design data.

Metrology system 100 can be operatively connected to one or more metrology tools 114. The term "Metrology tools" used herein should be expansively construed to cover any tools that can be used in metrology-related processes including, by way of non-limiting example, imaging, scanning (in a single or in multiple scans), sampling, reviewing, measuring, classifying and/or other processes provided with regard to the specimen or parts thereof. In some embodiments, metrology tools are configured to capture images and/or other representations of the specimen so as to provide the images and/or other representations to the metrology system 100 for metrology operations. Metrology system 100 can be further operatively connected to Design data server 110 (e.g., CAD server) which is configured to store and provide design data characterizing the specimen. In some cases, Metrology system 100 can be operatively connected to one or more Data repositories 116 which is configured to store data (and/or derivatives thereof) produced by the inspection tools 114 and/or the Design data server 110.

Metrology system 100 comprises a processing circuitry 102 operatively connected to a hardware-based I/O interface 120. Processing circuitry 102 is configured to provide all processing necessary for operating metrology system 100 which is further detailed with reference to FIGS. 2-3. Processing circuitry 102 comprises a processor (not shown separately) and a memory (not shown separately). The processor of processing circuitry 102 can be configured to execute several functional modules in accordance with computer-readable instructions implemented on a non-transitory computer-readable memory comprised in the processing circuitry. Such functional modules are referred to hereinafter as comprised in the processing circuitry 102.

Functional modules comprised in the processor can include a Mapping module 106, an Operation performing module 108 and optionally an Object and operation definition module 104, which are operatively connected with each other. Definitions of one or more metrology objects and one or more metrology operations can be accommodated in a memory (e.g., either in the memory as comprised in the Processing circuitry 102 or in the Storage unit 122). At least one of the group consisting of the one or more metrology objects and the one or more metrology operations can be defined with reference to design data. According to certain embodiments, the definitions of the metrology objects and metrology operations can be received from an external system or a storage device, or alternatively, the Object and operation definition module 104 as comprised in the processor can be configured to define the one or more metrology objects and the one or more metrology operations. The one or more metrology objects, and/or the metrology operations can be defined using, or with reference to design data.

In some embodiments, the metrology system 100 may be hosted by an metrology tool 114 and may be configured to operate with the hosting metrology tool and optionally with additional metrology tools. In some embodiments, the metrology system 100 may be integrated with metrology tool 114—in such embodiments, components of the metrology system 100 may form part of metrology tool 114. For example, processing circuitry 102 and storage unit 122 may form part of the processing circuitry and storage, respectively, of metrology tool 114 (not shown in FIG. 1); and the I/O interface and GUI of the metrology tool 114 (not shown in FIG. 1) may function as I/O interface 120 and GUI 124.

Metrology system 100 may be used for defining metrology objects and metrology operations. The metrology objects and metrology operations are defined with respect to representations of the specimen. In some embodiments, a user is presented with a representation of the specimen in a visual manner (for example, by a display forming part of GUI 124); the user may define metrology objects by selecting and/or marking metrology objects residing in the specimen representation—for example by operating a computer stylus or mouse. The user may further define metrology operations to be carried out with respect to the metrology objects, for example by selecting an option from a drop-down list.

A representation group comprising a design-based representation of the specimen and an image-based representation of the specimen can also be accommodated in the memory (e.g., either in the memory as comprised in the processing circuitry 102 or in the Storage unit 122). According to certain embodiments, the design-based representation (also referred to as design representation) of the specimen can comprise design-based representation of at least a first metrology object of the one or more metrology objects, and the image-based representation (also referred to as image representation) of the specimen can comprise image-based representation of the at least first metrology object of the one or more metrology objects. The image-based representation of the specimen can be image data resulted from imaging of the specimen, including one or more images of the specimen which can be received by system 100 from one or more metrology tools 114. The images can be resulted from different examination modality(s), and the present disclosure is not limited by the inspection and metrology technology used for generating the images. In certain embodiments, the images include inspection images. The design-based representation of the specimen can include design data characterizing the specimen, including one or more of the following: the physical design layout (e.g., CAD clip) of the specimen, a raster image and a simulated image derived from the design layout. It is to be noted that, unless specified otherwise, the terms "design data", "design-based representation" and "design representation" are used interchangeably within the present disclosure, as well as the terms "image data", "image-based representation" and "image representation" which are also used interchangeably within the present disclosure. In certain embodiments of the below description, image-based representation of a metrology object is also referred to as image metrology object or image object. Design-based representation of a metrology object is also referred to as design metrology object or design object.

The one or more metrology operations can include at least a first metrology operation. The at least first metrology operation can be defined to be related to the at least first metrology object and to be performed on at least the image-based representation of the specimen (e.g., related to the image-based representation of the at least first metrology object).

Mapping module 106 can be configured to map between the design-based representation of the at least first metrology object and the image-based representation of the at least first metrology object. Operation performing module 108 can be configured to perform the at least first metrology operation according to definition of the at least first metrology operation using the mapping. Operation of the metrology system 100, processing circuitry 102 and the functional blocks therein will be further detailed with reference to FIGS. 2-3. The terms "metrology object" or "object" used in this specification should be expansively construed to cover any metrology target as an element of a pattern in a layer on a semiconductor wafer under fabrication, that is defined on design data and/or image data. Metrology object(s) can be further defined according to different perspectives, such as, e.g., whether the metrology object has one representation or two corresponding representations, whether it is defined on design data or image data, whether it is an initial object or a derived object, and whether it is a structural element, a virtual object, a ghost object or any other kind of objects, etc., as will be described below in details with respect to FIG. 2.

The terms "metrology operation" or "operation" used in this specification should be expansively construed to cover any metrology operation procedure used to extract metrology information relating the metrology objects. By way of example, metrology information to be extracted can be indicative of region or object of interest, dimensions (line widths, line spacing, size of the element, edge roughness, gray level statistics, etc.) and/or shape of metrology objects and/or distances within or between metrology objects, related angles, and/or overlay information associated with metrology objects corresponding to different design levels, etc. The metrology operations can include measurement operations which in turn can include structure-based measurements, rule-based measurements, measurements based on templates, measurements associated with geometric properties such as distances and angles, and/or other measurements, as will be described in details below.

By way of example, the metrology objects and/or operations can be specified by a user via GUI 124. Alternatively or additionally, the metrology objects and/or operations can be resulted from an appropriate analysis of design data and/or image data. Optionally, a user can specify the metrology objects, while corresponding metrology operations can be, in response, automatically specified or selected, in accordance with predefined rules, among predefined operations associated to different metrology objects. In some cases, metrology objects can be specified in design coordinates. In other cases, metrology objects can be specified as structural elements characterized by shape, size and, optionally, location, geometrical relations between elements, relative position within the design representation or image representation. Further embodiments and examples with respect to metrology object and metrology operations are described below with respect to FIG. 2.

Metrology system 100 can be configured to receive, via I/O interface 102, data (and/or derivatives thereof) stored or produced by the metrology tools 114 and/or data stored in design data server 110 and/or data stored in one or more data repositories 116.

By way of example, a specimen can be inspected by an inspection machine. The resulting data and/or derivatives thereof) can be transmitted—directly or via one or more intermediate systems—to Metrology system 100. The present disclosure is not limited by the inspection technology. Non-limiting examples of inspection machines include scanning electron microscope (SEM), Tunneling Electron Microscope (TEM), optical metrology (OCD) or Atomic Force Microscopy (AFM)).

Metrology system 100 can be further configured to process the received image data provided by the metrology tools 114 and/or the design data provided by the design data server 110, and send, via I/O interface 102, the results (or part thereof) to a storage system which may be the same as the data repositories 116, or may be in addition or in lieu of the data repositories 116. The results can also be sent to any of the metrology tool(s) and/or an external system, and/or a computer-based graphical user interface (GUI) 124 for rendering the results. GUI 124 can be further configured to enable user-specified inputs related to Metrology system 100. In certain embodiments, GUI 124 can forming part of the metrology tool 114.

Those versed in the art will readily appreciate that the teachings of the presently disclosed subject matter are not bound by the system illustrated in FIG. 1; equivalent and/or modified functionality can be consolidated or divided in another manner and can be implemented in any appropriate combination of software with firmware and hardware.

It is noted that the metrology system illustrated in FIG. 1 can be implemented in a distributed computing environment, in which the aforementioned functional modules shown in FIG. 1 can be distributed over several local and/or remote devices, and can be linked through a communication network. It is further noted that although the metrology tools 114, data repositories 116, design data server 110 are illustrated as being external to the Metrology system 100 and operate in data communication with system 100 via I/O interface 120, in some other embodiments, at least part of the aforementioned units can be implemented as part of the Metrology system 100. For instance, Metrology system 100 can be implemented as stand-alone computer(s) to be used in conjunction with the metrology tools 114. Alternatively, the respective functions of system 100 can, at least partly, be integrated with one or more metrology tools 114. For instance, system 100 can be implemented as part of the metrology tools 114 thereby facilitating and enhancing the functionalities of the metrology tools 114 in metrology-related processes.

Figure 2:
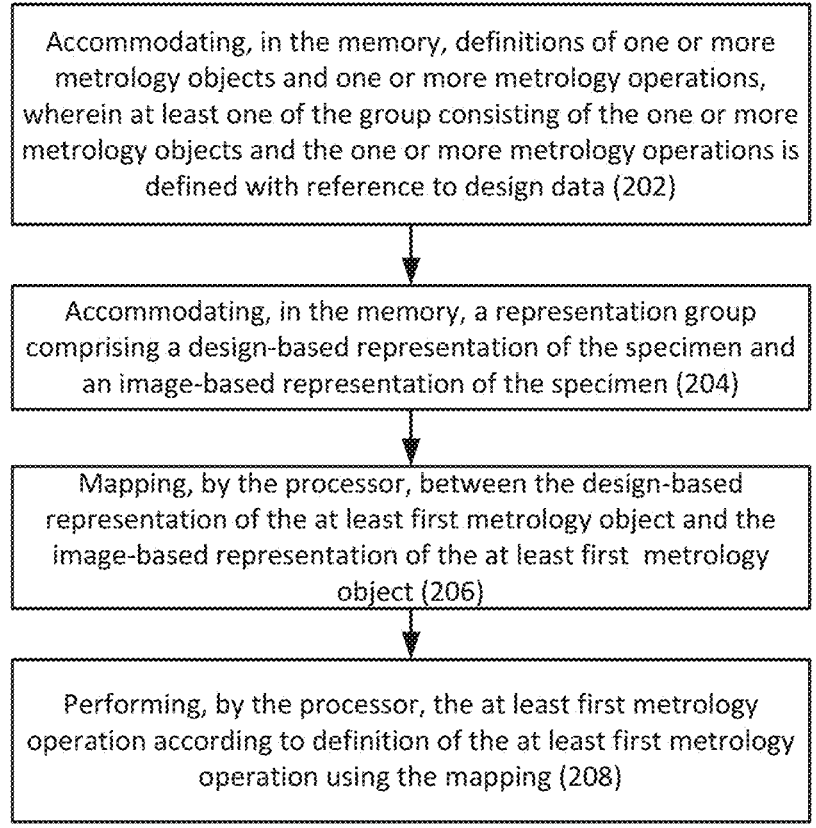
FIG. 2 illustrates a generalized flowchart of performing metrology operations on at least one representation of a specimen in accordance with certain embodiments of the presently disclosed subject matter.

Referring to FIG. 2, there is illustrated a generalized flowchart of performing metrology operations on at least one representation of a specimen in accordance with certain embodiments of the presently disclosed subject matter.

Definitions of one or more metrology objects and one or more metrology operations can be accommodated (202) in the memory (e.g., either in the memory as comprised in the processing circuitry 102 or in the Storage unit 122 as illustrated in FIG. 1). At least one of the group consisting of the one or more metrology objects and the one or more metrology operations can be defined using or with reference to design data.

For purpose of illustration only, certain embodiments of the following description are provided with respect to CAD clips. Embodiments are, likewise, applicable to other formats and representations of design data. In some embodiments (e.g. if design data are presented in vector format), intermediate processing of design data can be required.

As aforementioned, a metrology object can refer to any metrology target or element that is defined on design data and/or image data. Metrology object can be an object of interest or a pattern of interest to be measured. According to certain embodiments, the one or more metrology objects as defined can include one or more initial objects that are initially defined or identified on design data and/or image data. The one or more operations can include at least one operation defined related to the initial objects. By way of example, the initial objects can include an object of Field of View (FOV) indicative of the extent of observable range or scope on the design data and/or the image data within which subsequent objects and operations can be defined or performed. By way of another example, the initial objects can include one or more objects that originally exist on the design data and/or image data, such as, e.g., design structural elements on a CAD clip, and/or segmented structural elements obtained through a segmentation process on an inspection image. Such original objects can be specified by a user or automatically selected by the system as the initial objects.

A structural element used herein refers to any original object or element on the design data or image data that has a geometrical shape or geometrical structure with a contour, or a geometrical shape combined with insertion of other structural elements. A structural element that is located on the design data can be referred to as a design structural element. A design structural element can be presented, e.g., in the form of a polygon. A structural element that is located in the image data can be referred to as an image structural element. A structural element can be defined by the user, or can be defined automatically, for example using rule-based or machine-learning techniques.

According to certain embodiments, the one or more metrology objects can further include one or more derived objects that are resulted from performing at least one of the metrology operations defined related to the initial objects. The one or more metrology operations can include at least one operation defined related to the derived objects. By way of example, an initial object can be defined as FOV on the design data. An operation that is defined related to the initial object of FOV can be, e.g., a search operation which upon being performed can search for a specified design structural element or pattern of interest (e.g., a hotspot or other repetitive pattern to be measured) within the FOV. The search operation, once performed, may result in one or more structural elements or patterns of interest (if any) which meet the search query. These resulted objects are referred to as the derived objects, i.e., objects derived from performing metrology operations, as compared to the initial objects that are initially defined. Further metrology operations can in turn be defined related to the derived objects. For instance, an operation of Center of Gravity (CoG) can be defined related to the derived objects resulted from the search operation, e.g., the structural elements as being found. The CoG operation will result in an object which is derived therefrom, i.e., a center point of each structural element as being found. Note that objects such as, e.g., the center points, do not originally exist in the design data of the specimen and therefore are sometimes referred to as being "virtual".

It is to be noted that the term "virtual object" used herein should be expansively construed to cover any metrology object that does not have an original design-based representation thereof. Virtual objects can be defined on both design data or image data. According to certain embodiments, virtual objects can include derived objects that are resulted from performing operations and are not originally present in design data (e.g., the CoG objects as exemplified above).

Figure 4:
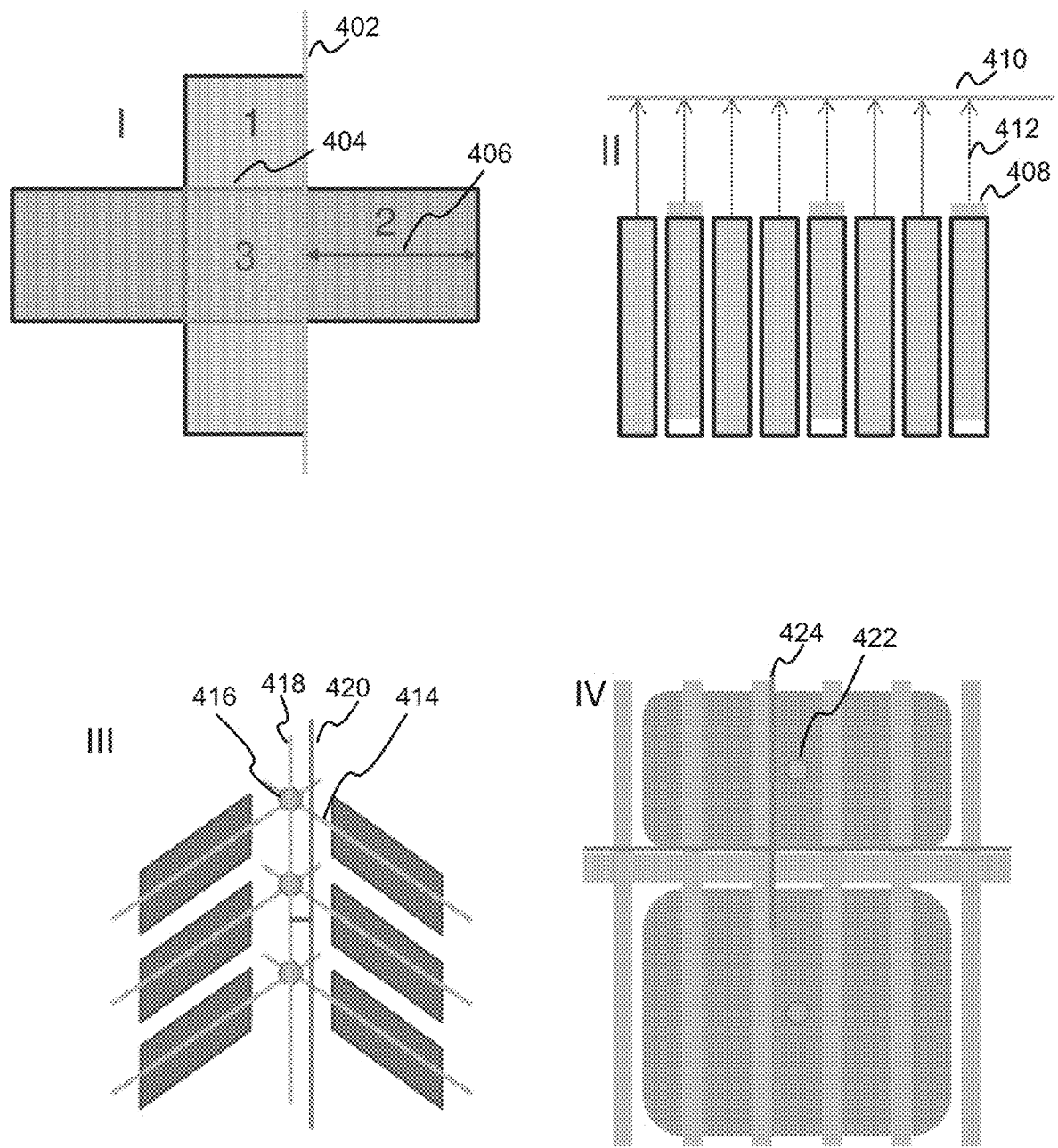
FIG. 4 illustrates examples of virtual objects in accordance with certain embodiments of the presently disclosed subject matter.

Turning now to FIG. 4, there are illustrated examples of virtual objects in accordance with certain embodiments of the presently disclosed subject matter. In graph I of FIG. 4, there are shown two intersected polygons which are originally present in a CAD clip: polygon 1 and polygon 2 as marked. A virtual object can be defined as a linear fit 402 to an edge (e.g., the right edge) of polygon 1. Another virtual object can be defined as the polygon 404 (i.e., the virtual rectangle 3 as marked) derived from the intersection of polygons 1 and 2. An operation of measurement, e.g., a distance 406 as shown in graph I can be defined with the assistance of the defined virtual objects. For instance, the distance 406 can be measured as a distance between the linear fit 402 and an edge of polygon 2. Alternatively, it can also be measured as a distance between the edge of polygon 404 and the edge of polygon 2. By way of another example, in graph II of FIG. 4, there are shown objects of rectangles 408 indicative of fins of a specimen. A virtual object can be defined as a virtual line 410 on design data, and an operation of measurement can be defined as a distance 412 between the upper edge of the rectangles 408 and the virtual line 410. As can be seen, graphs I and II illustrate virtual objects that are derived objects and are defined on design data.

By way of a further example, referring to graph III of FIG. 4, there are shown arrays of blobs on an inspection image. A virtual object can be defined as a major axis 414 identified for each blob. Another virtual object can be defined as an intersection point 416 of two adjacent major axes (resulted/derived from an operation of Finding intersection). A further virtual object can be a linear fit 418 resulted from an operation of Calculating linear fit of intersections on the inspection image. A similar virtual object can be defined as a linear fit 420 resulted from the same operation of Calculating linear fit of intersections but performed on the corresponding design data. A subsequent operation of calculating distance between the linear fit 418 and the linear fit 420 can result in a yet further virtual object of a distance (not shown in the graph). By way of yet a further example, graph IV shows another inspection image on which virtual objects of center point 422 (resulted from an operation of CoG) and linear fit 424 of an image object are defined. Further virtual objects can be defined as the corner of two linear fit as well as a distance between two objects of CoGs (not shown in the graph). As can be seen, graphs III and IV illustrate virtual objects that are derived objects and are defined on image data.

Accordingly, it can be arrived that derived objects can include structural elements that originally exist in a representation of the specimen (e.g., the objects resulted from a search operation), as well as virtual objects as defined above. Thus metrology objects can also be deemed as including structural elements and/or virtual objects. Metrology objects can also include ghost objects, as will be described in details below.

The process of objects being derived from operations and further operations being defined on the derived objects as described before can be repeated iteratively and such repetitive process is also referred to herein as "stack of operations".

In some embodiments, the definitions of one or more metrology operations can include where (i.e., on which representation) to perform the one or more metrology operations. This can be determined by one or more of the following factors: the type of the metrology operations, on which representation the metrology objects related to the metrology operations are defined and possibly one or more additional parameters defined by a user. By way of example, if a metrology object is defined as a polygon on a CAD clip, and the operation related to the object is Critical Dimension (CD), then the operation of CD can only be performed on the CAD clip, since the type of the operation CD determines that it will be performed at wherever the object is located. By way of another example, if a metrology object is defined as a structural element on the image, the operation related to the object is 'Distance from image to design', then this operation can be performed on both CAD and image, since the type of operation requires involvement of both CAD and image representation. By way of a further example, there may be such cases where based on the definition of the object and the type of operation related to the object, the operation should be performed on the image representation. However, there are provided more than one image representation as input, e.g., more than one inspection image are provided. In such cases, a user has the option to select among the inspection images and decide which image representation the operation will be performed on.

A representation group comprising a design-based representation of the specimen and an image-based representation of the specimen can also be accommodated (204) in the memory (e.g., either in the memory as comprised in the processing circuitry 102 or in the Storage unit 122 as illustrated in FIG. 1). The design-based representation of the specimen can comprise design-based representation of at least a first metrology object of the one or more metrology objects. The image-based representation of the specimen can comprise image-based representation of the at least first metrology object of the one or more metrology objects. In other words, the one or more metrology objects as defined can comprise at least one metrology object (i.e., the first metrology object) which has two corresponding representations: a design-based representation thereof on the design-based representation of the specimen (e.g., a CAD clip characterizing the specimen) and an image-based representation thereof on the image-based representation of the specimen (e.g., an inspection image of the specimen). The one or more metrology operations can include at least first metrology operation which is defined to be related to the at least first metrology object and to be performed on at least the image-based representation of the specimen.

According to certain embodiments, the design data used to define the one or more metrology objects and/or the one or more metrology operations can be the same as the design-based representation of the specimen to be measured or to be performed operations on. The one or more metrology operations can be defined related to at least one of the metrology objects. Accordingly, in such cases, each of the one or more metrology objects is defined either on the design-based representation of the specimen or on the image-based representation of the specimen.

In the cases where the one or more metrology objects are defined on the design-based representation of the specimen, the metrology operations, except for being defined as related to the metrology objects, can be further defined to be performed on the image-based representations of the specimen, or on both the image-based representations of the specimen and the design-based representation of the specimen. In the case that the one or more metrology objects are defined on the image-based representations of the specimen, the metrology operations, except for being defined as related to the metrology objects, can be further defined to be performed on the image-based representations of the specimen taking into consideration of the design-based representation of the specimen, or on both the image-based representations of the specimen and the design-based representation of the specimen.

According to some other embodiments, the design data used to define the one or more metrology objects and/or the one or more metrology operations is not necessarily the same as the design-based representation of the specimen to be measured or to be performed operations on. In one embodiment, the design data can be pre-acquired design data which is different from the design data of the specimen. For instance, the pre-acquired design data can be a representative design data or a reference design data provided for the purpose of defining the metrology objects and/or operations. Such pre-acquired design data may include different types (e.g., different shapes, sizes, etc.) of structural elements and/or patterns which, either individually or in appropriate combinations, can be used for defining the metrology objects. In such cases, the one or more metrology objects are defined on the pre-acquired design data, and at least one of the metrology operations is defined related to the one or more metrology objects.

It is to be noted that in such cases, since the design data of the specimen is different from the pre-acquired design data, it is possible that some of the defined metrology objects are not present in the design data of the specimen (for example, not present in a specific CAD clip). Therefore, a search on the design-based representation of the specimen can be performed in order to identify any metrology object of the defined one or more metrology objects that is present on the design-based representation of the specimen, i.e., the at least first metrology object of the one or more metrology objects as described above. For the identified objects resulted from the search, the operations defined as related to these objects are to be performed. For any metrology object that is defined in the pre-acquired design data but is not found in the design data of the specimen, the search result will return as null and thus no operations will be performed. One technical advantage of being able to define the metrology objects and/or operations on a pre-acquired design data is that, for a specific given metrology object, operations related thereto can be defined once and can be used with respect to different design data (e.g., CAD clips) of specimens, instead of defining the operations related to the same object each time when encountering such object in a different CAD clip. It is also to be noted that in this case some of the operations can be defined without relating to any objects, since when defining the operations, it is still unknown which metrology objects out of the defined objects may be present in the design data of the specimen. Therefore, an initial object such as a FOV object can be defined, and at least one operation can be defined related to the FOV object (e.g., a search operation). The subsequent operations can then be defined without reference to any specific object. For instance, a CD or a CoG operation can be defined to be performed on any object that may resulted from the search operation.

Similarly, in the above embodiments of defining the one or more metrology objects on a pre-acquired design data, the metrology operations can be defined to be performed on the image-based representations of the specimen, or on both the image-based representations of the specimen and the design-based representation of the specimen.

According to certain embodiments, the one or more metrology operations can be selected from a group comprising: Region of Interest (ROI) Operation, search operation, and measurement operation, etc. It is to be noted that although the operations of inspection/detection and segmentation are not explicitly listed here in the group, the output or results of these operations can be provided as initial objects for the metrology operations to be performed thereupon.

An operation of ROI can be defined as selecting a region or an area within the design data or image data for the purpose of performing subsequent operations. For instance, a ROI operation can result in a region within the FOV of a CAD clip for performing a subsequent search operation therein. The resulted region is sometimes also referred to as ROI. One example of a ROI can be a hotspot where, in view of design considerations, defects may occur at a higher probability thus require further inspection and measurement. Another example of a ROI can be a region informative of design layout of one or more different patterns of interest which can be specified or selected by a user or a design data processing unit.

A search operation is normally performed on design data and can be defined as searching for a specific object or an object of interest in a given region of the design data. By way of example, a search operation can be performed on an initial object, such as, e.g., the object of FOV as described above. By way of another example, a search operation can also be performed on the output of a preceding operation, such as, e.g., a ROI region resulted from ROI operation.

Figure 5:
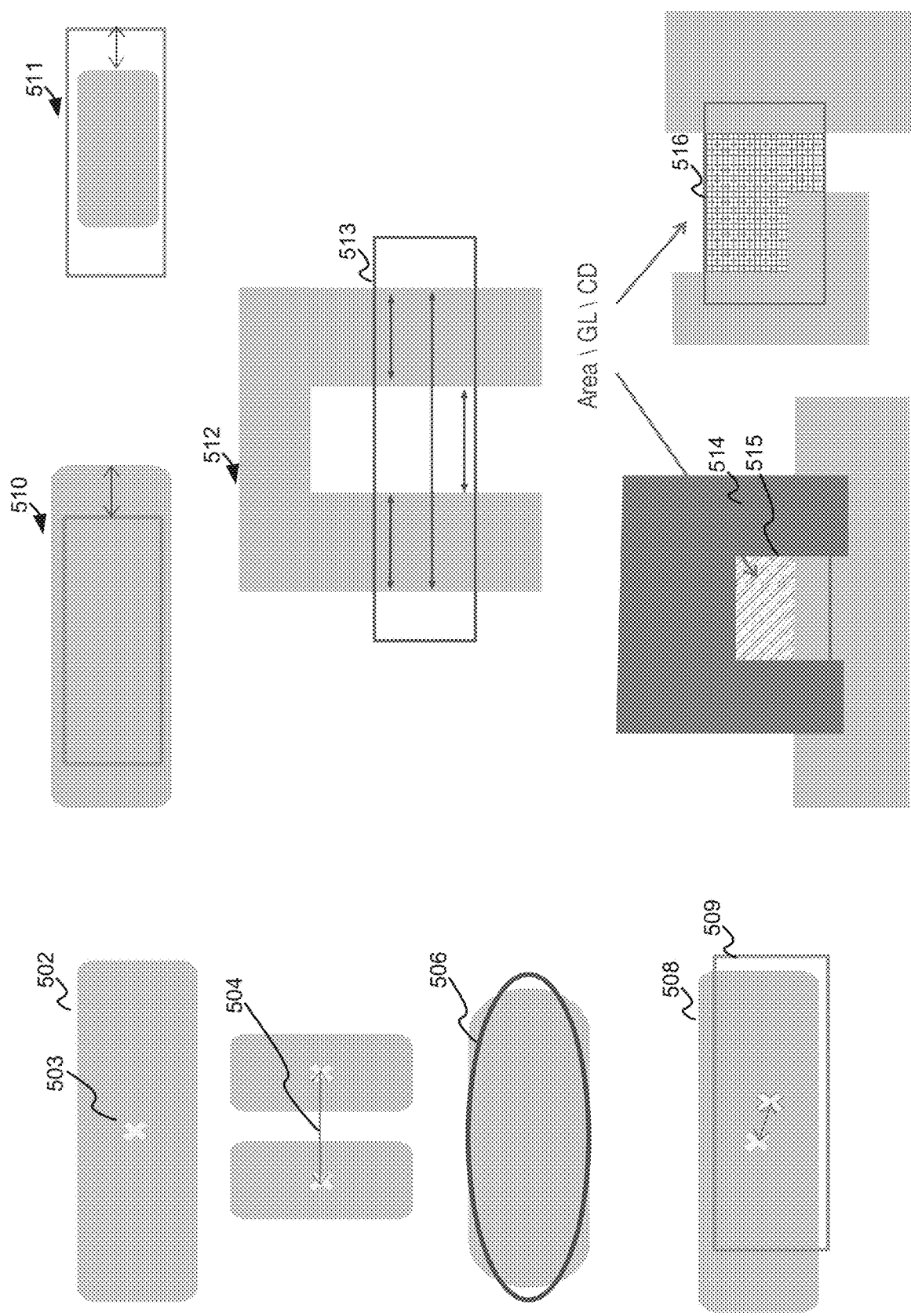
FIG. 5 illustrates examples of different types of measurement operations in accordance with certain embodiments of the presently disclosed subject matter.

A measurement operation should be expansively construed to cover any operation used to extract measurement information related to metrology objects. A measurement operation can be selected from a group comprising: Area of an object, Critical Dimension (CD)—length and width of dimensions of the object, Distance between objects, Center of Gravity (CoG) of an object, Gray Level (GL) statistics of an object, Contact Hole Analysis (CHA) of an object and additional shape-descriptors, 'Distance from image to design'—a comparison between design representation and image representation properties, and Arithmetic calculations, etc. Similarly, these terms can be used to refer to both the measurement operations and results of these operations. Turning now to FIG. 5, there are illustrated examples of different types of measurement operations in accordance with certain embodiments of the presently disclosed subject matter.

In one example, an operation of Center of Gravity (CoG) results in a point of CoG 502 which is the average location of the weight of an object 503. CoG refers the point at which weight of the object is evenly dispersed and all sides are in balance. The object 503 can be an object defined on the design data or on the image data. In another example, an operation of Distance between two CoGs is illustrated which results in the object of distance 504. In a further example, an operation of Contact Hole Analysis (CHA) can provide an output of an ellipse 506 that fit in the object in the shape of a polygon. In yet a further example, an operation of 'Distance from image to design' is exemplified as a distance between a CoG of an image-based representation 508 of an object and a CoG of a corresponding design-based representation 509 of the same object. The design-based representation 509 of the object is mapped with the corresponding image-based representation 508 and both representations are shown together in relative positions for the purpose of measuring the distance. The mapping process will be described in details below with reference to FIG. 3. Another example of 'Distance from image to design' is illustrated in 510 and 511 where a distance between an edge of a design object and an edge of a corresponding image object can be measured (namely, in 510 the design object falls within the image object and in 511 it is illustrated the other way around). In 512 there are illustrated operations of Critical Dimension (CD) related to a N-shaped polygon. CD refers to distances between borders or edges of an object or objects. As shown in 512, a ROI 513 is defined and four CDs are measured within the ROI 513. In yet a further example, within a ROI 514, a background area 515 formed by two surrounding polygons is illustrated, for which an operation of Area (which results in the size of the area) and an operation of Gray Level (GL) (which results in the value of the grayscale level of the area) can be performed. Within a ROI 516, a list of CDs (e.g., distances between edges of two polygons) can be measured. Operations of Arithmetic calculation (not illustrated in FIG. 5) can take one or more results of the measurement operations as inputs for performing arithmetic calculations thereupon (e.g., addition, subtraction, etc).

It is to be noted that the measurements shown in FIG. 5 are illustrated as non-limiting examples and are for the purpose of illustration only and should by no means be construed as limiting the present disclosure in any way. Other measurements or other examples of the above described measurements can be defined and performed in addition to or in lieu of the above.

Figure 3:
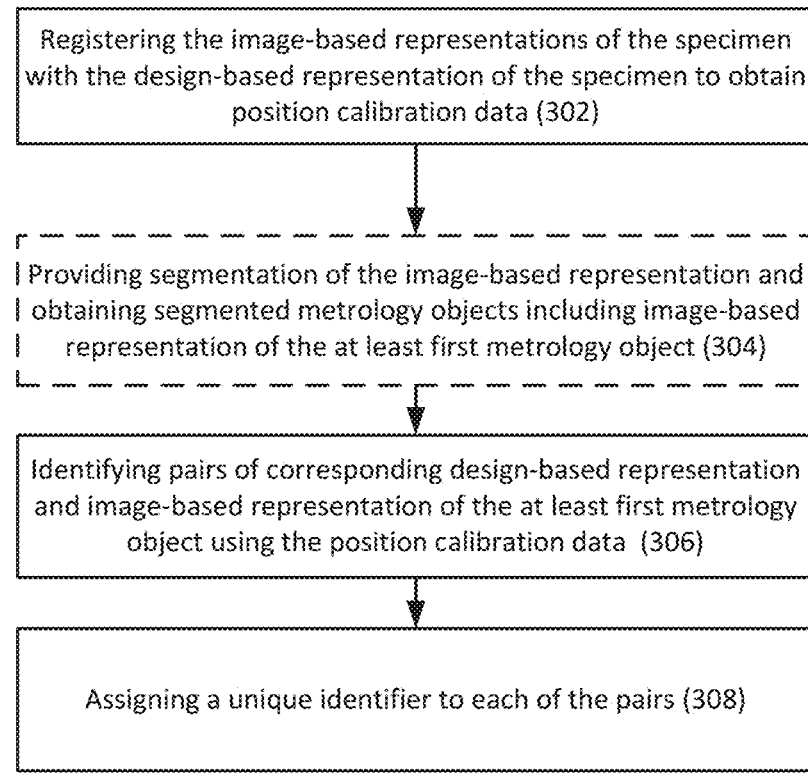
FIG. 3 illustrates a generalized flow chart of a mapping process in accordance with certain embodiments of the presently disclosed subject matter.

Continuing the process in FIG. 2, once the metrology objects and metrology operations are defined, and design-based representation and image based representation of the specimen are obtained, a mapping between the design-based representation of the at least first metrology object and the image-based representation of the at least first metrology object can be performed (206) (e.g., by the mapping module 106 illustrated in FIG. 1). Turning now to FIG. 3, there is provided a generalized flow chart of a mapping process in accordance with certain embodiments of the presently disclosed subject matter.

The image-based representations of the specimen can be registered (302) with the design-based representation of the specimen to obtain position calibration data. The mapping module 106 registers the image-based representations of the specimen (e.g., an inspection image) with regard to the corresponding design-based representation of the specimen (e.g., a CAD clip) thereby obtaining for the inspection image (or part thereof, e.g., ROI, or pattern of interest) coordinates in design space (coordinates in design space are referred to as design coordinates). Some differences between the coordinates of the inspection image and the corresponding locations in design coordinates are likely to occur for various reasons—scanning conditions (e.g. illumination) as well as imperfections, shifts and outright errors in the scanning process, errors in the manufacturing of the electric circuit printed on the wafer, and so forth.

The mapping module 106 further generates position calibration data. The position calibration data can be informative of a global (e.g. average) offset between the inspection image and design data and/or of multiple offsets, each related to a specific region or pattern or object of interest thereof. Optionally, the position calibration data can comprise a data structure specifying respective offsets for each object of interest (or groups thereof). The position calibration data can be stored in the memory as comprised in the processing circuitry 102 or the storage unit 122. The registration and position calibration generation process can be implemented according to any suitable method of registration algorithms known in the art (e.g. as described in US2007/0280527, US2013/204569 etc).

In cases where the at least first metrology objects is defined in design data, upon obtaining the image-based representation (e.g., the inspection image) of the specimen, the mapping module 106 further segments (304) the inspection image into groups of pixels belonging to the same object (or provides segmentation information of the inspection image), thereby identifying continuous regions corresponding to different metrology objects. Segmentation is provided to the inspection image or part thereof (e.g., the image area corresponding to the FOV or ROI) and is referred to as a global segmentation. The segmentation process can be implemented according to one or more similarity and/or discontinuity criteria and segmentation algorithm(s) known in the art, including, by way of example, histogram-based, edge-based, boundary-based, watershed and/or other segmentation algorithms. Through the segmentation, segmented metrology objects can be obtained (304) including the image-based representation of the at least first metrology object. Segmented metrology objects revealed by the segmentation can be stored in the memory as comprised in the processing circuitry 102 or in the storage unit 122. It is to be noted the step of segmentation is optional in some cases. For instance, if the metrology objects are originally defined on an inspection image, e.g., provided by an operation of segmentation or revealed by an inspection process, the step of segmentation can be omitted.

Pairs of corresponding design-based representation and image-based representation of the at least first metrology object can be identified (306) using the position calibration data and a unique identifier can be assigned (308) to each corresponding pair. By way of example, each design metrology object can be assigned with a unique identifier. For each given segmented metrology object, design coordinates of the inspection image (or part thereof) can be used for identifying a design metrology object corresponding to the segmented metrology object. Once identified, each segmented metrology object and pixels thereof can be assigned with the same unique identifier as of corresponding design metrology object. Alternatively, the identification process can start with assigning the unique identifier to a segmented metrology object, then using the position calibration data to identify a corresponding design metrology object which will then be assigned to the same unique identifier. An exemplified segmentation and mapping process is described in U.S. patent application Ser. No. 14/727,800 published on Dec. 1, 2016, which is incorporated herein in its entirety by reference.

It is to be noted that, except for the at least first metrology object that has both design and image representations, there may be certain metrology objects among the one or more metrology objects as defined which only have one representation (i.e., objects that only have design representation or image representation). For such objects, there may not be found any corresponding image or design representation thereof through the above mapping process. Therefore a different process is needed for performing operations related to these objects, as will be detailed below.

According to certain embodiments, the one or more metrology objects can include at least one metrology object (also referred to as at least a second metrology object, to be distinguished from other objects defined herein) which has only a design-based representation thereof on the design-based representation of the specimen (i.e., does not have image-based representation thereof). For instance, due to causes such as, e.g., manufacture error or scanning conditions etc., certain metrology objects that are present in the design data of a specimen may be absent in the corresponding image data of the specimen. Such objects that only have design representation are sometimes referred to as "ghost objects". At least one metrology operation of the one or more metrology operations (also referred to as at least a second metrology operation, to be distinguished from other operations defined herein) is defined as related to the at least second metrology object and to be performed on the image-based representation or on both the design-based representation of the specimen and the image-based representation.

For these objects, similarly as described with reference to block 302, the image-based representations of the specimen can be registered with the design-based representation of the specimen to obtain position calibration data. A position indication of the at least second metrology object on the image-based representation of the specimen can then be identified using the position calibration data. By way of example, the offset between the inspection image and design data can be used to find a relative position of the at least second metrology object on the inspection image as compared to the design representation thereof. The at least second metrology operation of the one or more metrology operations related to the at least second metrology object can be performed according to definition of the at least second metrology operation using the position indication. As aforementioned, the definition of the at least second metrology operation can determine that the at least second metrology operation can be performed on the image representation or on both image and design representation.

According to certain embodiments, the one or more metrology objects can include at least one defect object that has only an image-based representation thereof on the image-based representation of the specimen. For a defect object, since it is produced due to certain manufacture error in the manufacture process of the specimen, there is no corresponding design-based representation thereof on the original design data of the specimen. Metrology operations related to a defect object can be defined with reference to design data of the specimen.

In some further cases, at least one metrology operation of the one or more metrology operations (also referred to as at least a third metrology operation, to be distinguished from other operations defined herein) can be defined as related to the at least one defect object and to be performed on both the image-based representation and the design-based representation of the specimen. In such cases, similarly as described with reference to block 302, the image-based representations of the specimen can be registered with the design-based representation of the specimen to obtain position calibration data. A position indication of the at least one defect object on the design-based representation of the specimen can be identified using the position calibration data. By way of example, the offset between the inspection image and design data can be used to find a relative position of the at least one defect object on the design representation of the specimen as compared to the position of the at least one defect object on the image representation of the specimen. By way of another example, in cases where one or more neighboring metrology objects are present in the vicinity of the defect object on the image-based representation of the specimen which have corresponding design-based representation thereof on the design-based representation of the specimen, such neighboring metrology objects can be identified and mapped with the corresponding design-based representation thereof using position calibration data. A position indication of the at least one defect object on the design-based representation of the specimen can be identified using the design-based representation of the neighboring metrology objects as an anchor. The at least third metrology operation can then be performed on both the image-based representation and the design-based representation of the specimen using the position indication.

Figure 6:
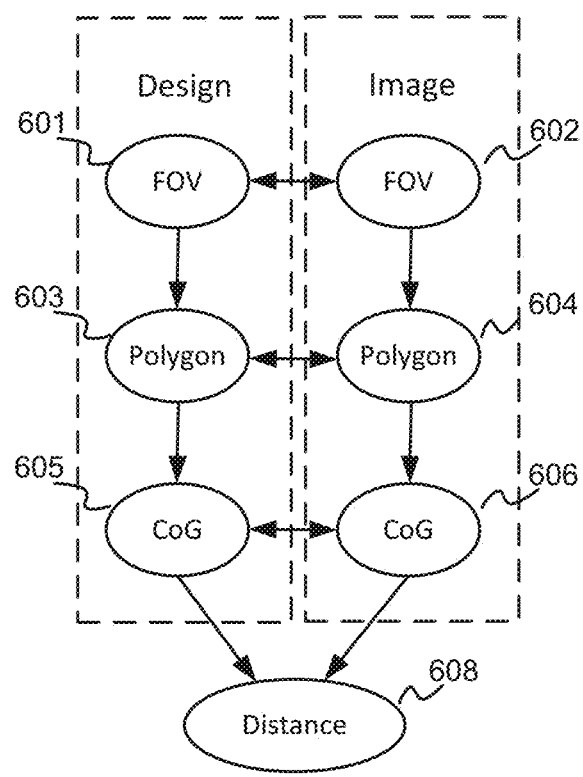
FIG. 6 illustrates an example of metrology objects associated with the attribute of context in accordance with certain embodiments of the presently disclosed subject matter.

According to certain embodiments, at least one of the metrology objects as defined can be associated with an attribute of context indicative of a parent object thereof. Turning now to FIG. 6, there is illustrated an example of metrology objects associated with the attribute of context in accordance with certain embodiments of the presently disclosed subject matter.

As shown, there are illustrated pairs of corresponding design representation and image representation of metrology objects (i.e., corresponding design objects and image objects) and sequence of operations related thereto. A design object of FOV 601 is defined on the design data of the specimen. A polygon 603 is identified within FOV 601 (e.g., through a search operation), and an object of CoG 605 can be resulted from an operation of CoG performed on the polygon 603. Similarly, on the corresponding image representation of the specimen, image objects of FOV 602, polygon 604 and CoG 606 are also defined which respectively correspond to FOV 601, polygon 603 and CoG 605. An object of Distance 608 between two CoGs 606 and 608 can be resulted from performing an operation of 'Distance from image to design' on the two CoGs. By way of example, the object of Distance 608 can have an attribute of context associated therewith indicating that Distance 608 is related to polygons 603 and 604 (e.g., polygons 603 and 604 are parents objects of Distance 608). The attribute of context can be identified through sequence of operations. The parents objects associated therewith can include direct parent objects and/or indirect parent objects. For a given object, with which parent objects to associate as context can depend on the type of the object. In some cases, a given object may not have a parent object thereof (e.g., the object of FOV). In that case, the context of the given object can be itself. In some embodiments, the attribute of context can form part of the definition of the metrology objects and can be used to report result of the metrology operations from which the metrology objects are derived.

Referring back to the process of FIG. 2, the at least first metrology operation of the one or more metrology operations related to the at least first metrology object can be performed (208) (e.g., by the Operation performing module 108 illustrated in FIG. 1) according to definition of the at least first metrology operation using the mapping. The at least first metrology operation is defined to be related to the at least first metrology object and to be performed on at least the image-based representation of the specimen. In some embodiments, the definition of the at least first metrology operation can also include where (e.g., which representation(s)) to perform such operation, which is determined by one or more of the following factors: the type of the metrology operations, a representation where the metrology objects related to the metrology operations are defined and one or more additional parameters defined by a user, as described above. Therefore, when performing the at least first metrology operation, the Operation performing module 108 can obtain the information of where to perform the operation from the definition of the operation, and perform the operation on the representation(s) as defined. By way of example, when the metrology objects are defined on the design-based representation of the specimen, the metrology operations related thereto are defined to be performed on the image-based representations of the specimen, or on both the image-based representations of the specimen and the design-based representation of the specimen. When the one or more metrology objects are defined on the image-based representations of the specimen, the metrology operations are defined to be performed on both the image-based representations of the specimen and the design-based representation of the specimen. Thus the mapping process as described above with reference to FIG. 3 is needed when performing the metrology operations since the definition of metrology object and the performing of the metrology operations together require both representations of the metrology objects.

Referring back to the system of FIG. 1: using GUI 124, a user may select metrology objects and metrology operations, to thereby generate a metrology recipe ('recipe set up'). During recipe set up, the metrology tool may perform measurements in accordance with the defined metrology objects and metrology operations, and a decision to accept or refine the definition of such metrology objects and metrology operations based on respective measurement results, may be received by a user or in an automated manner Once a metrology recipe is defined, the metrology tool 114 may implement the metrology recipe and performs measurements on plurality of specimen ('run time'). The metrology results may be presented via GUI 124.

It is to be noted that the examples and embodiments described herein are illustrated as non-limiting examples and should not be construed to limit the presently disclosed subject matter in any way.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer-readable storage medium tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

What is claimed is:

1. A system comprising:
a memory; and
a processor, operatively coupled with the memory, to:
identify one or more metrology objects and one or more metrology operations;
receive a design-based representation of a first metrology object of the one or more metrology objects;
receive an image-based representation of the first metrology object of the one or more metrology objects, and wherein the one or more metrology operations include a first metrology operation associated with the first metrology object;
determining whether the first metrology operation is to be performed with either the design-based representation of the first metrology object or the image-based representation of the first metrology object or whether the first metrology operation is to be performed with both of the design-based representation of the first metrology object and the image-based representation of the first metrology object; and
in response to determining that the first metrology operation is to be performed with both of the design-based representation of the first metrology object and the image-based representation of the first metrology object:
map the design-based representation of the first metrology object with the image-based representation of the first metrology object; and
perform the first metrology operation based on the mapping.

2. The system of claim 1, wherein each of the one or more metrology objects corresponds to an element or a pattern of a layer of a semiconductor wafer.

3. The system of claim 1, wherein the first metrology operation corresponds to a measurement of a dimension of the first metrology object.

4. The system of claim 1, wherein the processor is further to:
provide a graphical user interface (GUI) of a plurality of metrology objects on a visual representation of a semiconductor wafer; and
receive a selection of the one or more metrology objects from the plurality of metrology objects on the visual representation of the semiconductor wafer.

5. The system of claim 1, wherein the processor is further to:
identify one or more virtual metrology objects, wherein each of the one or more virtual metrology objects is not specified by a particular design-based representation of a semiconductor wafer.

6. The system of claim 5, wherein the one or more virtual metrology objects are based on objects specified by the particular design-based representation of the semiconductor wafer.

7. The system of claim 5, wherein the one or more virtual metrology objects are selected by a user.

8. A method comprising:
identifying one or more metrology objects and one or more metrology operations;
receiving a design-based representation of a first metrology object of the one or more metrology objects;
receiving an image-based representation of the first metrology object of the one or more metrology objects, and wherein the one or more metrology operations include a first metrology operation associated with the first metrology object;

determining whether the first metrology operation is to be performed with either the design-based representation of the first metrology object or the image-based representation of the first metrology object or whether the first metrology operation is to be performed with both of the design-based representation of the first metrology object and the image-based representation of the first metrology object; and in response to determining that the first metrology operation is to be performed with both of the design-based representation of the first metrology object and the image-based representation of the first metrology object:

mapping, by a processing device, the design-based representation of the first metrology object with the image-based representation of the first metrology object; and performing the first metrology operation based on the mapping.

9. The method of claim 8, wherein each of the one or more metrology objects corresponds to an element or a pattern of a layer of a semiconductor wafer.

10. The method of claim 8, wherein the first metrology operation corresponds to a measurement of a dimension of the first metrology object.

11. The method of claim 8, wherein the method further comprises:

providing a graphical user interface (GUI) of a plurality of metrology objects on a visual representation of a semiconductor wafer; and receiving a selection of the one or more metrology objects from the plurality of metrology objects on the visual representation of the semiconductor wafer.

12. The method of claim 8, wherein the method further comprises:

identifying one or more virtual metrology objects, wherein each of the one or more virtual metrology objects is not specified by a particular design-based representation of a semiconductor wafer.

13. The method of claim 12, wherein the one or more virtual metrology objects are based on objects specified by the particular design-based representation of the semiconductor wafer.

14. The method of claim 12, wherein the one or more virtual metrology objects are selected by a user.

15. A non-transitory computer readable medium comprising instructions, which when executed by a processor, cause the processor to perform operations comprising:

identifying one or more metrology objects and one or more metrology operations;

receiving a design-based representation of a first metrology object of the one or more metrology objects;

receiving an image-based representation of the first metrology object of the one or more metrology objects, and wherein the one or more metrology operations include a first metrology operation associated with the first metrology object;

determining whether the first metrology operation is to be performed with either the design-based representation of the first metrology object or the image-based representation of the first metrology object or whether the first metrology operation is to be performed with both of the design-based representation of the first metrology object and the image-based representation of the first metrology object;

in response to determining that the first metrology operation is to be performed with both of the design-based representation of the first metrology object and the image-based representation of the first metrology object:

mapping, by the processing device, the design-based representation of the first metrology object with the image-based representation of the first metrology object; and performing the first metrology operation based on the mapping.

16. The non-transitory computer readable medium of claim 15, wherein each of the one or more metrology objects corresponds to an element or a pattern of a layer of a semiconductor wafer.

17. The non-transitory computer readable medium of claim 15, wherein the first metrology operation corresponds to a measurement of a dimension of the first metrology object.

18. The non-transitory computer readable medium of claim 15, wherein the operations further comprise:

providing a graphical user interface (GUI) of a plurality of metrology objects on a visual representation of a semiconductor wafer; and receiving a selection of the one or more metrology objects from the plurality of metrology objects on the visual representation of the semiconductor wafer.

19. The non-transitory computer readable medium of claim 8, wherein the operations further comprise:

identifying one or more virtual metrology objects, wherein each of the one or more virtual metrology objects is not specified by a particular design-based representation of a semiconductor wafer.

20. The non-transitory computer readable medium of claim 19, wherein the one or more virtual metrology objects are based on objects specified by the particular design-based representation of the semiconductor wafer.

* * * * *